(12) United States Patent
Kunin

(10) Patent No.: US 9,155,915 B2
(45) Date of Patent: Oct. 13, 2015

(54) MOISTURIZING RETINOL COMPOSITION

(75) Inventor: Audrey Kunin, Mission Hills, KS (US)

(73) Assignee: DERMADOCTOR, INC., Kansas City, MO (US)

( * ) Notice: Subject to any disclaimer, the term of this patent is extended or adjusted under 35 U.S.C. 154(b) by 400 days.

(21) Appl. No.: 12/844,368

(22) Filed: Jul. 27, 2010

(65) Prior Publication Data

US 2011/0020414 A1    Jan. 27, 2011

Related U.S. Application Data

(60) Provisional application No. 61/228,788, filed on Jul. 27, 2009.

(51) Int. Cl.
| | | |
|---|---|---|
| *A61K 36/185* | (2006.01) | |
| *A61Q 19/00* | (2006.01) | |
| *A61K 33/30* | (2006.01) | |
| *A61K 36/38* | (2006.01) | |
| *A61K 36/68* | (2006.01) | |
| *A61K 31/65* | (2006.01) | |
| *A61K 31/19* | (2006.01) | |
| *A61K 8/38* | (2006.01) | |
| *A61Q 19/08* | (2006.01) | |
| *A61K 8/11* | (2006.01) | |
| *A61K 8/67* | (2006.01) | |

(52) U.S. Cl.
CPC . *A61Q 19/08* (2013.01); *A61K 8/11* (2013.01); *A61K 8/671* (2013.01); *A61K 2800/412* (2013.01); *A61K 2800/522* (2013.01); *A61K 2800/75* (2013.01)

(58) Field of Classification Search
None
See application file for complete search history.

(56) References Cited

U.S. PATENT DOCUMENTS

| 6,231,877 | B1 * | 5/2001 | Vacher et al. | 424/401 |
| 6,846,812 | B2 * | 1/2005 | Dalko et al. | 514/171 |
| 7,700,110 | B2 * | 4/2010 | Zimmerman et al. | 424/195.15 |
| 8,084,062 | B2 * | 12/2011 | Kang et al. | 424/725 |
| 2003/0232091 | A1 * | 12/2003 | Shefer et al. | 424/490 |
| 2005/0164991 | A1 * | 7/2005 | Dalko et al. | 514/125 |
| 2006/0198800 | A1 * | 9/2006 | Dilallo et al. | 424/59 |
| 2008/0183250 | A1 * | 7/2008 | Tanojo et al. | 607/88 |
| 2008/0292734 | A1 * | 11/2008 | Hill | 424/738 |
| 2009/0130040 | A1 * | 5/2009 | Jonchiere | 424/62 |
| 2010/0034758 | A1 * | 2/2010 | Majeed et al. | 424/59 |
| 2011/0086060 | A1 * | 4/2011 | Bidamant et al. | 424/195.17 |

FOREIGN PATENT DOCUMENTS

FR    2814070 A1 *  3/2002

OTHER PUBLICATIONS

Pompei et al. Glycyrrhizic acid inhibits virus growth and inactivates virus particles, Nature vol. 281, Oct. 1979).*

* cited by examiner

*Primary Examiner* — Michael G Hartley
*Assistant Examiner* — Nabila Ebrahim
(74) *Attorney, Agent, or Firm* — Husch Blackwell LLP

(57) ABSTRACT

An anti-aging composition is provided that contains high potency retinol along with anti-irritant properties. In particular, an anti-aging composition includes a base, from about 0.001% to 20.0 vol % retinol, at least one anti-irritant agent, at least one antioxidant, at least one anti-inflammatory agent, and a moisturizing complex. In one non-limiting illustration, the anti-aging composition contains about 1.0 vol % retinol, *plantago lanceolata*, *hypericum perforatum* leaf extract, phytosphingosine, *leontopodium alpinum* extract, *glycyrriza glabra* root extract, *sambucus nigra* flower extract, nordihydrognaiaretic acid, oleanolic acid, *spiraea ulmaria* flower extract, *evodia rutaecarpa* fruit extract, *boswellia serrata* extract, and additives.

2 Claims, No Drawings

MOISTURIZING RETINOL COMPOSITION

CROSS-REFERENCE TO RELATED APPLICATIONS

This application is a nonprovisional of and claims priority to the U.S. Provisional Patent Application Ser. No. 61/228,788, filed Jul. 27, 2009, which document is hereby incorporated by reference in its entirety to the extent permitted by law.

BACKGROUND OF THE INVENTION

The condition and appearance of skin degenerates through the effects of environmental and other factors, such as, for example, sunlight, wind abrasion, humidity, pollutants, diseases, and/or the normal aging process. Common problems for aging skin are the formation of wrinkles, fine lines, age spots, enlarged pores, blotchy skin discoloration, surface roughness, loss of elasticity, and drooping skin.

To prevent or repair the deterioration of skin quality that occurs over time, consumers have increasingly sought new and/or improved products for skin care. Such products are designed to prevent, delay or reverse the visible signs of the aging process, such as the appearance of wrinkles and fine lines, loss of skin tone, thinning of the skin, hyperpigmentation or mottling, and age spots. These products may also improve the appearance and condition of sensitive, dry or flaky skin, and may soothe skin that has been irritated by exposure to chemicals, wind, or sunlight, among other potential irritants.

There are many different over-the-counter and prescription products available to treat the signs of aging and promote healthier skin. Some of these products contain retinoic acid, a topical Vitamin A derivative that is available by prescription to treat the signs of aging. Retinol is also found in some products to treat the signs of aging and is available without a prescription. Retinoic acid is twenty percent stronger than retinol so to be effective a higher potency of retinol is used in over-the-counter products. However, most products that contain retinoic acid or high potency retinol currently available lead to inadequate results or have undesirable side effects. These side effects may include, but not limited to, irritation, redness, stinging, itching, blistering, burning, skin scaling, peeling and dryness of the skin, or more severe side effects including, but not limited to, severe burning, itching, blistering, crusting, or swelling of the skin, alterations in skin pigmentation, or aggravate eczema. By peeling of the top layer of skin, retinoids may increase ones sensitivity to sunlight. Irritation may also be aggravated by wind or cold, use of soaps and cleansers, astringents, peeling agents and certain cosmetics.

Therefore, it would be beneficial to have a topical skin care treatment that contains an effective amount of retinol to prevent or repair the effects of aging, reduces fine lines, repairs skin discoloration, and rejuvenates the skin with the least possible side effects. It would also be beneficial to have a skin care treatment that contains high potency retinol that also reduces harmful side effects. It would be further beneficial to have a topical skin care treatment that has an anti-irritant complex to reduce the side effects and concerns associated with the use of retinol.

Retinoids have been used extensively in the treatment of a variety of skin disorders and have been used as skin repair or renewal agents. Topical retinoids are typically creams, lotions or gels containing retinol (Vitamin A) or related compounds. Topical retinoids are often effective treatment for mild to severe acne. People that are prone to acne have to be careful what type of lotions and creams they use so as to not make their acne worse. In addition to the above-mentioned side effects, a user may also develop irritation to the skin or adjacent mucous membranes and the production of excessive oiliness or greasiness of the skin which can clog pores. Therefore, it would be beneficial to have a skin care treatment that contains potent retinol that will not clog pores.

SUMMARY OF THE INVENTION

The present invention is generally directed to an anti-aging composition. The anti-aging composition hereof contains about 1 vol % retinol along with anti-irritant properties. In particular, one embodiment of the anti-aging composition of the present invention includes a base, about 1 vol % retinol, at least one anti-irritant agent, at least one antioxidant, at least one anti-inflammatory agent, and a moisturizing complex. In another non-limiting illustration, the anti-aging composition contains about 1% retinol, *plantago lanceolata, hypericum perforatum* leaf extract, phytosphingosine, *leontopodium alpinum* extract, glycyrriza *glabra* root extract, *sambucus nigra* flower extract, nordihydroguiaretic acid, oleanolic acid, *spiraea ulmaria* flower extract, *evodia rutaecarpa* fruit extract, *boswellia serrata* extract, and additives.

Other and further objects of the invention, together with the features of novelty appurtenant thereto, will appear in the course of the following description.

DETAILED DESCRIPTION OF THE INVENTION

There is provided herein a high potency topical retinol anti-aging composition that provides intensive action against the signs of aging while actively protecting against redness, dryness and irritation. The anti-aging composition hereof generally includes a base, about 1 vol % retinal, at least one anti-irritant, at least one antioxidant, at least one anti-inflammatory agent, and a moisturizing complex. It will be appreciated by those skilled in the art that some agents disclosed throughout may have two or more properties.

The composition of the present invention is designed to maximize skin rejuvenation with the least possible side effects. In certain embodiments, the retinol is present in an amount of from about 0.001 to 20.0 vol % of the composition, more preferably from about 0.1 to 10.0 vol %, and most preferably from about 1.0 vol %. In one embodiment, the composition contains the highest potency pure retinol (1%) available to provide intensive action. In an alternative embodiment, the retinol is microencapsulated that results in a slow release to ensure greater bioavailability.

In one embodiment, the anti-aging composition includes an effective amount of a base. In certain embodiments, the base is present in an amount from about 0.01 to 99.9 vol % of the composition. Preferred bases include, but are not limited to, lotions, creams, solutions, ointments, and washes.

In one embodiment, the anti-aging composition may also include an effective amount of an anti-irritant. In certain embodiments, the anti-irritant is present in an amount of from about 0.001 to 80.0 vol % of the composition, more preferably from about 0.01 to 50.0 vol %, and most preferably from about 0.1 to 5.0 vol %. In certain other embodiments, the anti-irritant is *plantago lanceolata, hypericum perforatum* leaf extract, phytosphingosine, derivatives thereof, or mixtures thereof. *Plantago lanceolata* is a perennial found in the mountains of Switzerland containing properties that enhance collagen production and wound healing and is both an antioxidant and an anti-irritant. *Hypericum perforatum* leaf extract also known as St. John's Wort is a source of powerful irritation-soothing flavonoids including quercetin. Phytosphingosine is a naturally-occurring skin lipid with anti-redness and skin firming properties.

In one embodiment of the present invention, the anti-aging composition also includes an effective amount of an antioxidant. In certain embodiments, the antioxidant is present in an amount of from about 0.001 to 80.0 vol % of the composition, more preferably from about 0.01 to 50.0 vol %, and most preferably from about 0.1 to 5.0 vol %. In certain other embodiments, the antioxidant is *plantago lanceolata, leontopodium alpinum* extract, *glycyrriza glabra* root extract, *sambucus nigra* flower extract, derivates thereof, or mixtures thereof. *Leontopodium alpinum* extract is an alpine flower extract that has antioxidant and free radical-scavenging properties. *Glycyrriza glabra* root extract also known as licorice root extract is an antioxidant with skin-soothing properties. *Sambucus nigra* flower extract is an antioxidant rich in bioflavonoids and anthocyanins.

In addition to the antioxidants named herein above, other antioxidants suitable for use in the present composition include brompheniramine maleate, diclofenac, carbenoxolone sodium, chlorpheniramine maleate, dexbrompheniramine, diphenhydramine hydrochloride, diphenylpyraline hydrochloride, doxylamine succinate, cetirizine HCL, cinnarazine, chlorphenhydramine maleate, naphazoline hydrochloride, pheniramine maleate, famotidine, flufenazine hydrochloride, ketotifen, omeprazole, pantoprazole sodium, ranitidine, cimetidine, cyproheptadine, clemastine, hydroxyzine pamoate, doxepin HCL, loratadine, mebhydrolin naphthalenesulfonate, methapyrilene hydrochloride, orphenadrine citrate, pheniramine maleate, pyrilamine maleate, meclizine, quetiapine, ranitidine, terfenadine, thonzylamine hydrochloride, experimental H-3 and H-4 antagonists, for example, ABT-239, cipralisant, ciproxifan, clobenpropit, and thioperamide, derivatives thereof, and mixtures thereof.

In one embodiment of the present invention, the anti-aging composition also includes an effective amount of an anti-inflammatory agent. In certain embodiments, the anti-inflammatory agent is present in an amount of from about 0.001 to 80.0 vol % of the composition, more preferably from about 0.01 to 50.0 vol %, and most preferably from about 0.1 to 10.0 vol %. In certain other embodiments, the anti-inflammatory agent is nordihydrognaiaretic acid, oleanolic acid, *spiraea ulmaria* flower extract, *evodia rutaecarpa* fruit extract, *boswellia serrata* extract, derivates thereof, or mixtures thereof. Nordihydrognaiaretic acid and oleanolic acid target redness while calming inflammation. *Spiraea ulmaria* flower extract also known as meadowsweet has both anti-inflammatory and antiseptic benefits. *Evodia rutaecarpa* fruit extract also known as Wu Zhu Yu is a berry extract native to China shown to have a calming effect on inflammation in human skin. *Boswellia serrata* extract also known as Indian Frankincense has shown to have soothing effect on inflammation in human skin.

In one embodiment of the present invention, the anti-aging composition also includes an effective amount of an anti-inflammatory agent. In certain embodiments, the anti-inflammatory agent is present in an amount of from about 0.001 to 80.0 vol % of the composition, more preferably from about 0.01 to 50.0 vol %, and most preferably from about 0.1 to 10.0 vol %. In certain other embodiments, the anti-inflammatory agent is nordihydroguiaretic acid, oleanolic acid, *spiraea ulmaria* flower extract, *evodia rutaecarpa* fruit extract, *boswellia serrata* extract, derivates thereof, or mixtures thereof. Nordihydroguiaretic acid and oleanolic acid target redness while calming inflammation. *Spiraea ulmaria* flower extract also known as meadowsweet has both anti-inflammatory and antiseptic benefits. *Evodia rutaecarpa* fruit extract also known as Wu Zhu Yu is a berry extract native to China shown to have a calming effect on inflammation in human skin. *Boswellia serrata* extract also known as Indian Frankincense has shown to have soothing effect on inflammation in human skin.

In one embodiment of the present invention, the anti-aging composition also includes an effective amount of a moisturizing complex. In certain embodiments, the moisturizing complex is present in an amount of from about 0.001 to 80.0 vol % of the composition, more preferably from about 0.01 to 50.0 vol %, and most preferably from about 1.0 to 20.0 vol %. In certain other embodiments the moisturizing complex includes cyclomethicone, safflower seed oil, hyalurouic acid, shea butter, glycerin, bisabolol, oat kernel extract, ceramide-2, derivatives thereof, and mixtures thereof. The moisturizing complex establishes a protective barrier and inhibits dryness and peeling that may be associated with topical retinol use.

In certain embodiments, the anti-aging composition may also include from about 0.01% to about 80.0% of an additive such as fragrance, caprylic/capric triglyceride, glycerin, glyceryl acrylate, acrylic acid copolymer, cyclopentasiloxane, dimethicone crosspolymer, stearic acid, glyceryl stearate, cyclomethicone, *carthamus tinctorius* (safflower) seed oil, stearyl alcohol, *butyrospermum parkii* (shea butter), polysorbate 60, sorbitol, phenoxyethanol, caprylyl glycol, ethylhexyl glycerin, hexylene glycol, allyl methacrylates crosspolymer, polysorbate 20, butylene glycol, PEG-60 almond glycerides, carbomer, dimethicone, caffeine, bisabolol, dipotassium glycyrrhizate, tea carbomer, sodium hyaluronate, sodium benzoate, potassium sorbate, *chamomilla recutita* (chamomile) matricaria extract, *cucumis sativus* (cucumber) fruit extract, ceramide 2, PEG-40 hydrogenated castor oil, *panax ginseng* root extract, *avena sativa* (oat) kernel extract, *curcuma longa* (turmeric) root extract, BHT, *malva sylvestris* (mallow) flower extract, *salvia officinalis* (sage) leaf extract, *centella asiatica* extract, leucine, valine, tyrosine, arginine, and lysine.

In one embodiment, the anti-aging composition hereof includes about 1.0% retinol, 5.0% caprylic/capric triglyceride, 3.5% glycerin, 3.5% glyceryl acrylate, 3.5% acrylic acid copolymer, 3.5% cyclopentasiloxane, 3.5% dimethicone crosspolymer, 3.25% stearic acid, 2.5% glyceryl stearate, 2.5% cyclomethicone, 2.0% *carthamus tinctorius* (safflower) seed oil, 1.75% stearyl alcohol, 1.5% *butyrospermum parkii* (shea butter), 1.5% polysorbate 60, 1.0% sorbitol, 1.0% phenoxyethanol, 1.0% caprylyl glycol, 1.0% ethylhexyl glycerin, 1.0% hexylene glycol, 1.0% allyl methacrylates crosspolymer, 1.0% polysorbate 20, 0.5% butylene glycol, 0.5% PEG-60 almond glycerides, 0.5% carbomer, 0.5% nordihydroguaiaretic acid, 0.5% oleanolic acid, 0.5% dimethicone, 0.5% phytosphingosine, 0.5% caffeine, 0.5% bisabolol, 0.5% dipotassium glycyrrhizate, 0.5% tea carbomer, 0.5% sodium hyaluronate, 0.25% *leontopodium alpinum* (edelweiss) extract, 0.25% *plantago lanceolata* leaf extract, 0.25% sodium benzoate, 0.25% potassium sorbate, 0.1% *evodia rutaecarpa* fruit extract, 0.1% *boswellia serrata* extract, 0.1% *glycyrrhiza glabra* (licorice) root extract, 0.1% *chamomilla recutita* (chamomile) matricaria extract, 0.1% *cucumis sativus* (cucumber) fruit extract, 0.1% ceramide 2, 0.1% PEG-40 hydrogenated castor oil, 0.1% *panax ginseng* root extract, 0.1% *avena sativa* (oat) kernel extract, 0.1% *curcuma longa* (turmeric) root extract, 0.1% BHT, 0.1% *hypericum perforatum* (St. John's Wort) leaf extract, 0.1% *malva sylvestris* (mallow) flower extract, 0.1% *salvia officinalis* (sage) leaf extract, 0.1% *sambucus nigra* (elderberry) flower extract, 0.1% *spiraea ulmaria* (meadowsweet) flower extract, 0.1% *centella asiatica* extract, 0.1% leucine, 0.1% valine, 0.1% tyrosine, 0.1% arginine, 0.1% lysine, and deionized water.

Clinical Study

One embodiment of the present invention was clinically tested to demonstrate that a user, having applied the composition to the skin, developed few, if any, side effects even though the composition contained about 1% retinol. The standards used for inclusion in the study included individuals who were not currently under a doctor's care; individuals who were free of any dermatological or systemic disorder that would interfere with the results; individuals who were free of any acute or chronic disease that would interfere with or increase the risk of study participation; individuals who completed a preliminary medical history form mandated by BCS and were in generally good health; individuals who read, understood and signed an informed consent document relating to the specific type of study; and individuals who were able to cooperate with the investigator and research staff, were willing to have test materials applied according to the study protocol, and completed the full course of the study. The standards for exclusion from the study were individuals who were under 18 years of age; individuals who were currently under a doctor's care; individuals who were currently taking any medication (topical or systemic) that might mask or interfere with the test results; individuals who had a history of any acute or chronic disease that might interfere with or increase the risk associated with study participation; individuals who were diagnosed with chronic skin allergies; and female volunteers who indicated that they were pregnant or nursing. Fifty-five subjects were enrolled in the study and fifty-three completed the study. The subjects ranged in age from eighteen to fifty-nine. The population demographics of the study were seven males and forty-six females.

Test materials to be tested under occlusive conditions were placed on an 8-millimeter aluminum chamber supported on a sheet of occlusive tape or an equivalent thereof. Test materials to be tested under semi-occlusive conditions were placed on sensitive skin bandages. Test materials to be tested in an open patch were applied and rubbed directly onto the back of the subject. Approximately 0.02-0.05 mL (in case of liquids) and/or 0.02-0.05 gm (in case of solids) of the test material was used for the study. Liquid test material was dispensed on a 7.5 mm paper disk that fit in the aluminum chamber.

The following procedure was followed by the subjects. Subjects were requested to bathe or wash as usual before arrival at the facility. Patches containing the test material were then affixed directly to the skin of the intrascapular regions of the back, to the right or left of the midline, and subjects were dismissed with instructions not to wet the test area or expose it to direct sunlight. Subjects were instructed to remove the patches approximately 24 hours after application. This procedure was repeated until a series of nine (9) consecutive, 24-hour exposures had been made three (3) times a week for three (3) consecutive weeks. Prior to each reapplication, the test sites were evaluated by trained laboratory personnel. Following a 10-14 day rest period, a retest/challenge dose was applied once to a previously unexposed test site. Test sites were evaluated by trained laboratory personnel 48 and 96 hours after application. In the event of an adverse reaction, the area of erythema and edema were measured. Edema is estimated by the evaluation of the skin with respect to the contour of the unaffected normal skin. Subjects were instructed to report any delayed reactions that might occur after the final reading.

The following scoring system was used and the scoring scale and definition of symbols shown below are based on the scoring scheme according to the International Contact Dermatitis Research Group (ICDRG)[*Contact Dermatitis, Dermatology, Volume 1, 2nd edition, by S Moschella M D, H Hurley M D, W.B Saunders, Company, 1985.*]:

0 No visible reaction, doubtful reaction

1 A weak (nonvesicular) reactions showing mild erythema (redness) and possible papules (small elevated lesions, granular feeling)

2 A strong reaction (moderate erythema) with vesicles (small elevated lesions that are fluid filled, <=5 mm)

3 Severe (bright red) erythema with extreme blistering

D Site discontinued

Dc Subject discontinued

NOTE: Clinical evaluations were performed by a BCS investigator or designee trained in the clinical evaluation of the skin. Whenever feasible, the same individual conducted the scoring of all the subjects throughout the study and was blinded to the treatment assignments and any previous scores.

A summary of the results is shown in Table 1:

TABLE 1

| | Subject Information | | | | Induction | | | | | | | | | Challenge | |
|---|---|---|---|---|---|---|---|---|---|---|---|---|---|---|---|
| No. | ID | Sex | Age | Race | 1 | 2 | 3 | 4 | 5 | 6 | 7 | 8 | 9 | 1 | 2 |
| 1 | 101 | F | 49 | H | 0 | 0 | 0 | 0 | 0 | 0 | 0 | 0 | 1 | 0 | 0 |
| 2 | 102 | F | 31 | H | 0 | 0 | 0 | 0 | 0 | 0 | 0 | 0 | 0 | 0 | 0 |
| 3 | 103 | F | 52 | H | 0 | 0 | 0 | 0 | 0 | 0 | 0 | 0 | 0 | 0 | 0 |
| 4 | 104 | F | 22 | H | 0 | 0 | 0 | 0 | 0 | 0 | 0 | 0 | 0 | 0 | 0 |
| 5 | 105 | F | 51 | H | 0 | 0 | 0 | 0 | 0 | 1 | 1 | 1 | 1 | 0 | 0 |
| 6 | 106 | F | 18 | H | 0 | 0 | 0 | 0 | 0 | 0 | 0 | 0 | 0 | 0 | 0 |
| 7 | 107 | F | 43 | H | 0 | 0 | 0 | 0 | 0 | 0 | 0 | 0 | 1 | 0 | 0 |
| 8 | 108 | F | 18 | H | 0 | 0 | 0 | 0 | 0 | 0 | 0 | 0 | 0 | 0 | 0 |
| 9 | 109 | M | 36 | H | 0 | 0 | 0 | 0 | 0 | 0 | 0 | 0 | 0 | 0 | 0 |
| 10 | 110 | F | 31 | H | 0 | 0 | 0 | 0 | 0 | 0 | 0 | 0 | 0 | 0 | 0 |
| 11 | 111 | F | 38 | H | 0 | 0 | 0 | 0 | 0 | 0 | 0 | 1 | 1 | 0 | 0 |
| 12 | 112 | M | 33 | H | 0 | 0 | 0 | 0 | 0 | 1 | 0 | 0 | 0 | 0 | 0 |
| 13 | 113 | F | 37 | H | 0 | 0 | 0 | 0 | 0 | 0 | 0 | 0 | 2 | 2 | 0 |
| 14 | 114 | F | 40 | H | 0 | 0 | 0 | 0 | 0 | 0 | 0 | 0 | 0 | 0 | 0 |
| 15 | 115 | F | 29 | H | 0 | 0 | 0 | 0 | 0 | 0 | 0 | 0 | 0 | 0 | 0 |
| 16 | 116 | F | 27 | H | 0 | 0 | 0 | 0 | 0 | 0 | 1 | 0 | 0 | 0 | 0 |
| 17 | 117 | F | 44 | H | 0 | 0 | 0 | 0 | 0 | 0 | 0 | 0 | 0 | 0 | 0 |
| 18 | 118 | F | 25 | H | 0 | 0 | 0 | 0 | 0 | 0 | 0 | 0 | 0 | 0 | 0 |
| 19 | 119 | F | 31 | H | 0 | 0 | 0 | 0 | 0 | 0 | 0 | 0 | 0 | 0 | 0 |
| 20 | 121 | F | 49 | H | 0 | 0 | 0 | 0 | 0 | 0 | 0 | 0 | 0 | 0 | 0 |
| 21 | 122 | F | 47 | H | 0 | 0 | 0 | 0 | 0 | 0 | 0 | 0 | 0 | 0 | 0 |

TABLE 1-continued

| | Subject Information | | | | Induction | | | | | | | | | Challenge | |
|---|---|---|---|---|---|---|---|---|---|---|---|---|---|---|---|
| No. | ID | Sex | Age | Race | 1 | 2 | 3 | 4 | 5 | 6 | 7 | 8 | 9 | 1 | 2 |
| 22 | 123 | F | 54 | H | 0 | 0 | 0 | 0 | 0 | 0 | 0 | 0 | 1 | 0 | 0 |
| 23 | 124 | F | 42 | H | 0 | 0 | 0 | 0 | 0 | 0 | 0 | 0 | 0 | 0 | 0 |
| 24 | 125 | M | 36 | H | 0 | 0 | 0 | 0 | 0 | 0 | 0 | 0 | 0 | 0 | 0 |
| 25 | 126 | F | 22 | H | 0 | 0 | 0 | 0 | 0 | 0 | 0 | 0 | 0 | 0 | 0 |
| 26 | 127 | F | 58 | H | 0 | 0 | 0 | 0 | 0 | 0 | 0 | 0 | 0 | 0 | 0 |
| 27 | 128 | F | 36 | H | 0 | 0 | 0 | 0 | 0 | 1 | 0 | 0 | 1 | 0 | 0 |
| 28 | 130 | F | 58 | H | 0 | 0 | 0 | 1 | 0 | 0 | 0 | 0 | 0 | 0 | 0 |
| 29 | 131 | M | 25 | H | 0 | 0 | 0 | 0 | 0 | 0 | 0 | 0 | 0 | 0 | 0 |
| 30 | 132 | F | 27 | H | 0 | 0 | 0 | 0 | 0 | 0 | 0 | 0 | 0 | 0 | 0 |
| 31 | 133 | F | 28 | H | 0 | 0 | 0 | 0 | 0 | 0 | 0 | 0 | 0 | 0 | 0 |
| 32 | 134 | F | 27 | H | 0 | 0 | 0 | 0 | 0 | 0 | 0 | 0 | 0 | 0 | 0 |
| 33 | 135 | F | 25 | H | 0 | 0 | 0 | 0 | 0 | 0 | 0 | 0 | 0 | 0 | 0 |
| 34 | 136 | F | 37 | H | 0 | 0 | 0 | 0 | 0 | 0 | 0 | 0 | 0 | 0 | 0 |
| 35 | 137 | F | 34 | H | 0 | 0 | 0 | 0 | 0 | 0 | 0 | 0 | 0 | 0 | 0 |
| 36 | 138 | F | 59 | H | 0 | 0 | 0 | 0 | 0 | 0 | 0 | 0 | 0 | 0 | 0 |
| 37 | 139 | F | 50 | H | 0 | 0 | 0 | 0 | 1 | 1 | 1 | 1 | 1 | 1 | 0 |
| 38 | 140 | F | 43 | H | 0 | 0 | 0 | 0 | 0 | 0 | 0 | 0 | 0 | 0 | 0 |
| 39 | 141 | F | 40 | H | 0 | 0 | 0 | 0 | 0 | 0 | 0 | 0 | 0 | 0 | 0 |
| 40 | 142 | F | 43 | H | 0 | 0 | 0 | 1 | 1 | 1 | 1 | 1 | 1 | 0 | 0 |
| 41 | 143 | F | 31 | H | 0 | 0 | 0 | 0 | 0 | 0 | 0 | 0 | 0 | 0 | 0 |
| 42 | 144 | F | 32 | H | 0 | 0 | 0 | 0 | 0 | 0 | 0 | 1 | 1 | 0 | 0 |
| 43 | 145 | F | 40 | H | 0 | 0 | 0 | 0 | 0 | 0 | 0 | 0 | 0 | 0 | 0 |
| 44 | 146 | F | 50 | H | 0 | 0 | 0 | 0 | 1 | 1 | 0 | 0 | 0 | 0 | 0 |
| 45 | 147 | F | 23 | H | 0 | 0 | 0 | 0 | 0 | 0 | 0 | 0 | 0 | 0 | 0 |
| 46 | 148 | F | 18 | H | 0 | 0 | 0 | 0 | 0 | 0 | 0 | 0 | 0 | 0 | 0 |
| 47 | 149 | F | 30 | H | 0 | 0 | 0 | 0 | 0 | 0 | 0 | 0 | 0 | 0 | 0 |
| 48 | 150 | F | 53 | H | 0 | 0 | 0 | 1 | 1 | 1 | 1 | 1 | 1 | 0 | 0 |
| 49 | 151 | M | 30 | H | 0 | 0 | 0 | 0 | 0 | 0 | 0 | 0 | 0 | 0 | 0 |
| 50 | 152 | F | 41 | H | 0 | 0 | 0 | 0 | 0 | 0 | 0 | 0 | 0 | 0 | 0 |
| 51 | 153 | M | 41 | H | 0 | 0 | 0 | 0 | 0 | 0 | 0 | 0 | 0 | 0 | 0 |
| 52 | 154 | F | 21 | H | 0 | 0 | 0 | 0 | 0 | 0 | 0 | 0 | 0 | 0 | 0 |
| 53 | 155 | M | 22 | H | 0 | 0 | 0 | 0 | 0 | 0 | 0 | 0 | 0 | 0 | 0 |

The clinical study provided the observation that there were no adverse reactions of any kind reported during the course of the study. The study concluded that, under the conditions of the study, there were no identifiable signs or symptoms of sensitization (contact allergy) noted for the 1% retinol cream tested.

From the foregoing, it will be seen that this invention is one well adapted to attain all ends and objects hereinabove set forth together with the other advantages which are obvious and which are inherent to the composition. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative, and not in a limiting sense.

What is claimed is:

1. A topical anti-aging and substantially non-irritating composition consisting essentially of:
   a cosmetic lotion containing therein;
   about 1 vol % retinol;
   about 0.25 vol % *leontopodium alpinum* extract;
   about 0.1 vol % *hypericum perforatum* leaf extract;
   about 0.1 vol % *sambucus nigra* flower extract;
   about 0.5 vol % nordihydroguaiaretic acid;
   about 0.5 vol % oleanolic acid;
   about 0.1 vol % *malva sylvestris* flower extract;
   about 0.1 vol % *spiraea ulmaria* flower extract;
   about 0.1 vol % *evodia rutaecarpa* fruit extract;
   about 0.1 vol % *boswellia serrata* extract;
   about 0.5 vol % phytosphingosine;
   about 5.0 vol % caprylic/capric triglyceride;
   about 3.5 vol % glycerin;
   about 3.5 vol % glyceryl acrylate;
   about 3.5 vol % acrylic acid copolymer;
   about 3.5 vol % cyclopentasiloxane;
   about 3.5 vol % dimethicone crosspolymer;
   about 3.25 vol % stearic acid;
   about 2.5 vol % glyceryl stearate;
   about 2.5 vol % cyclomethicone;
   about 2.0 vol % *carthamus tinctorius* (safflower) seed oil;
   about 1.75 vol % stearyl alcohol;
   about 1.5 vol % *butyrospermum parkii* (shea butter);
   about 1.5 vol % polysorbate 60;
   about 1.0 vol % sorbitol;
   about 1.0 vol % phenoxyethanol;
   about 1.0 vol % caprylyl glycol;
   about 1.0 vol % ethylhexyl glycerin;
   about 1.0 vol % hexylene glycol;
   about 1.0 vol % allyl methacrylates crosspolymer;
   about 1.0 vol % polysorbate 20;
   about 0.5 vol % butylene glycol;
   about 0.5 vol % PEG-60 almond glycerides;
   about 0.5 vol % carbomer;
   about 0.5 vol % dimethicone;
   about 0.5 vol % caffeine;
   about 0.5 vol % bisabolol;
   about 0.5 vol % dipotassium glycyrrhizate;
   about 0.5 vol % tea carbomer;
   about 0.5 vol % sodium hyaluronate;
   about 0.25 vol % sodium benzoate;
   about 0.25 vol % potassium sorbate;
   about 0.25 vol % *plantago lanceolata* leaf extract;
   about 0.1 vol % *glycyrrhiza glabra* root extract;
   about 0.1 vol % *chamomilla recutita* (chamomile) matricaria extract;
   about 0.1 vol % *cucumis sativus* (cucumber) fruit extract;

about 0.1 vol % ceramide 2;
about 0.1 vol % PEG-40 hydrogenated castor oil;
about 0.1 vol % *panax ginseng* root extract;
about 0.1 vol % *avena sativa* (oat) kernel extract;
about 0.1 vol % *curcuma longa* (turmeric) root extract;
about 0.1 vol % BHT;
about 0.1 vol % *salvia officinalis* (sage) leaf extract;
about 0.1 vol % *centella asiatica* extract;
about 0.1 vol % leucine;
about 0.1 vol % valine;
about 0.1 vol % tyrosine;
about 0.1 vol % arginine;
about 0.1 vol % lysine; and
about 45.3 vol % deionized water.

2. A topical anti-aging and substantially non-irritating composition consisting essentially of:
a cosmetic lotion containing therein:
about 1% w/w retinol;
about 0.25% w/w *leontopodium alpinum* extract;
about 0.1% w/w *hypericum perforatum* leaf extract;
about 0.1% w/w *sambucus nigra* flower extract;
about 0.5% w/w nordihydroguaiaretic acid;
about 0.5% w/w oleanolic acid;
about 0.1% w/w *malva sylvestris* flower extract;
about 0.1% w/w *spiraea ulmaria* flower extract;
about 0.1% w/w *evodia rutaecarpa* fruit extract;
about 0.1% w/w *boswellia serrata* extract;
about 0.5% w/w phytosphingosine;
about 5.0% w/w caprylic/capric triglyceride;
about 3.5% w/w glycerin;
about 3.5% w/w glyceryl acrylate;
about 3.5% w/w acrylic acid copolymer;
about 3.5% w/w cyclopentasiloxane;
about 3.5% w/w dimethicone crosspolymer;
about 3.25% w/w stearic acid;
about 2.5% w/w glyceryl stearate;
about 2.5% w/w cyclomethicone;
about 2.0% w/w *carthamus tinctorius* (safflower) seed oil;
about 1.75% w/w stearyl alcohol;
about 1.5% w/w *butyrospermum parkii* (shea butter);
about 1.5% w/w polysorbate 60;
about 1.0% w/w sorbitol;
about 1.0% w/w phenoxyethanol;
about 1.0% w/w caprylyl glycol;
about 1.0% w/w ethylhexyl glycerin;
about 1.0% w/w hexylene glycol;
about 1.0% w/w allyl methacrylates crosspolymer;
about 1.0% w/w polysorbate 20;
about 0.5% w/w butylene glycol;
about 0.5% w/w PEG-60 almond glycerides;
about 0.5% w/w carbomer;
about 0.5% w/w dimethicone;
about 0.5% w/w caffeine;
about 0.5% w/w bisabolol;
about 0.5% w/w dipotassium glycyrrhizate;
about 0.5% w/w tea carbomer;
about 0.5% w/w sodium hyaluronate;
about 0.25% w/w sodium benzoate;
about 0.25% w/w potassium sorbate;
about 0.25% w/w *plantago lanceolata* leaf extract;
about 0.1% w/w *glycyrrhiza glabra* root extract;
about 0.1% w/w *chamomilla recutita* (chamomile) matricaria extract;
about 0.1% w/w *cucumis sativus* (cucumber) fruit extract;
about 0.1% w/w ceramide 2;
about 0.1% w/w PEG-40 hydrogenated castor oil;
about 0.1% w/w *panax ginseng* root extract;
about 0.1% w/w *avena sativa* (oat) kernel extract;
about 0.1% w/w *curcuma longa* (turmeric) root extract;
about 0.1% w/w BHT;
about 0.1% w/w *salvia officinalis* (sage) leaf extract;
about 0.1% w/w *centella asiatica* extract;
about 0.1% w/w leucine;
about 0.1% w/w valine;
about 0.1% w/w tyrosine;
about 0.1% w/w arginine;
about 0.1% w/w lysine; and
about 45.3% w/w deionized water.

* * * * *